United States Patent [19]
Kuo

[11] Patent Number: 5,876,944
[45] Date of Patent: Mar. 2, 1999

[54] METHOD FOR AMPLIFICATION OF THE RESPONSE SIGNAL IN A SANDWICH IMMUNOASSAY

[75] Inventor: Hai-Hang Kuo, Granger, Ind.

[73] Assignee: Bayer Corporation, Elkhart, Ind.

[21] Appl. No.: 660,923

[22] Filed: Jun. 10, 1996

[51] Int. Cl.⁶ .................................................. G01N 33/53
[52] U.S. Cl. ......................... 435/7.1; 436/510; 436/814; 436/65; 436/88; 436/170; 422/56; 422/60
[58] Field of Search ............................... 435/7.1; 436/510, 436/814, 65, 88, 170; 422/56, 60

[56] References Cited

U.S. PATENT DOCUMENTS

| | | |
|---|---|---|
| 4,474,892 | 10/1984 | Murad et al. . |
| 4,703,017 | 10/1987 | Campbell et al. . |
| 5,326,707 | 7/1994 | Franke et al. . |

FOREIGN PATENT DOCUMENTS

| | | |
|---|---|---|
| 0299428 | 7/1988 | European Pat. Off. . |
| 2204398 | 11/1988 | United Kingdom . |

OTHER PUBLICATIONS

Weir et al (Editors) "Handbook of Experimental Immunology, vol. 1: Immunochemistry" Blackwell Scientific Publications, USA pp. 35.24–35.25, 1986.

*Primary Examiner*—Paula K. Hutzell
*Assistant Examiner*—Heather A. Bakalyar
*Attorney, Agent, or Firm*—Jerome L. Jeffers

[57] ABSTRACT

Disclosed is an improvement to a sandwich type immunoassay in which there is immobilized to a solid support an antibody which is specific to an epitope of the analyte whose presence or concentration is being sought and a first labeled antibody which is specific to another epitope of the analyte. The improvement involves providing a second labeled antibody which is specific to the first labeled antibody to thereby form a chain of two or more labeled antibodies which results in amplification of the signal generated upon formation of the sandwich.

24 Claims, 2 Drawing Sheets

METHOD FOR AMPLIFICATION OF THE RESPONSE SIGNAL IN A SANDWICH IMMUNOASSAY

BACKGROUND OF THE INVENTION

Sandwich type immunoassays in which there is immobilized to a solid substrate a first antibody which is specific for a first epitope of an analyte whose presence or concentration is being sought and a second labeled antibody specific for a second epitope of the analyte are well known. This type of assay can be run in microtitre plates or in a strip format where the fluid being tested for the analyte is applied to one end of a porous strip and allowed to flow through the various regions of the strip by capillarity. The analyte is bound to the immobilized antibody and the labeled antibody to complete the "sandwich". The label, referred to herein as the "signal generator" can be an enzyme which is reactive with a substrate to provide a colored response. Chromophores and fluorofores are also known signal generators. In U.S. Pat. No. 4,703,017 there is disclosed an immunoassay technique in which the signal generator is a particulate label which can be a liposome or microcapsule containing a visible dye which is visually detectable upon being bound to the first immobilized antibody via the analyte. Other signal generators include colloidal sized metal particles, such as gold sol, to which antibodies are bound.

The signal generated by the label on the analyte bound antibody is not always as strong as might be desired, and methods to amplify the signal have been proposed One such method, disclosed in U.S. Pat. No. 4,657,853 involves a method for producing a polymericenzyme/antibody conjugate by covalently coupling at least two enzyme molecules to produce a prepolymerized enzyme and then covalently coupling the prepolymerized enzyme to an antibody or antibody fragment.

In EP 0 516 529 $A_2$, there is disclosed an agglutination type immunoassay in which an antibody having three or more binding sites to a specific antibody being assayed to thereby amplify the agglutination so that the detection sensitivity for the antibody is improved.

In published Japanese application 5-322893 there is disclosed an amplification system in which antibodies specific for the analyte and antibodies specific for a different epitope of the analyte bearing enzymes as the signal generator are combined in solution. In addition there are included antibodies whose Fab portions are each specific for the enzyme signal generator which facilitate the formation of chains of the enzyme bearing antibodies which result in signal amplification when the chain of enzyme labeled antibodies is contacted with a suitable substrate.

SUMMARY OF THE INVENTION

The present invention is an improvement to a sandwich type immunoassay in which there is immobilized to a solid support a first antibody which is specific for a first epitope of an analyte whose presence or concentration is being sought. Included in the test medium is a primary signal generator which has bound to it at least one second antibody which is specific to a second epitope of the analyte. According to the improvement of the present invention there is included in the test medium a secondary signal generator having attached to it at least one antibody which is specific for the second antibody attached to the primary signal generator. This secondary signal generator binds to the second antibody attached to the primary signal generator to thereby amplify the signal generated by the assay. Since there are two antigen binding sites in a complete antibody, one copy of the antibody specific for the second antibody is sufficient for the formation of chains. Preferably, there are multiple copies of these antibodies attached to the primary and secondary signal generators in order to increase the chance of crosslinking.

BRIEF DESCRIPTION OF THE DRAWING

FIG. 2 represents an assay strip suitable for use in the present invention.

DESCRIPTION OF THE INVENTION

Figure 1:
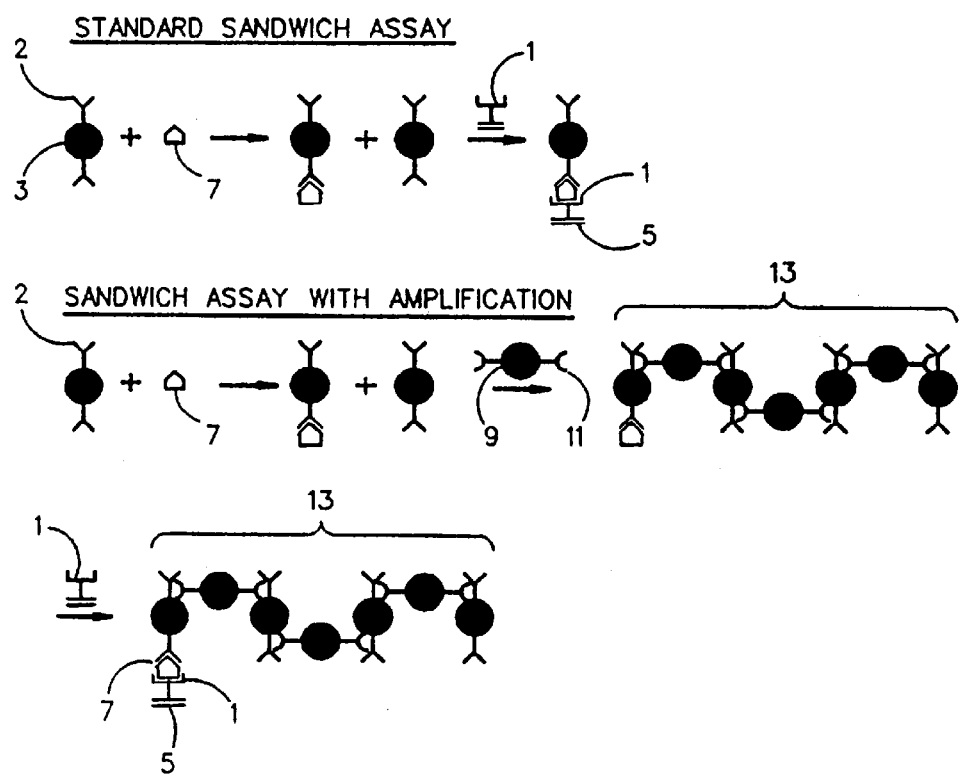
In FIG. 1, there is illustrated a conventional sandwich immunoassay and an amplified sandwich assay according to the present invention.

Referring to FIG. 1, in the standard sandwich assay, two sequential immunochemical reactions are carried out with separate antibodies that are specific to different epitopes of the analyte. The first antibody (Ab1), designated as 1 in the Figure, is immobilized to a solid support 5. The second antibody (Ab2) is labeled with a primary signal generator 3. When antibodies 1 and 2 react with these separate epitopes, the analyte is trapped between these antibodies in a sandwich configuration. By immobilizing first antibody 1 in a discrete capture zone, the signal produced by the primary signal generator 3 is concentrated in the capture zone where its detection indicates the presence of the analyte in the test fluid.

In the amplified sandwich assay, there is included in the reaction medium a secondary signal generator which can be the same as the primary signal generator 9 having attached to it at least one antibody (Ab3) 11 which is specific for the second antibody 2 attached to the primary signal generator 3. This antibody can be specific for either the light chain or the heavy chain of the second antibody provided that it is not specific to the parts of those chains which comprise the antigen binding sites. It is preferred that it be specific to the heavy chain because the light chain is relatively short and the interaction between Ab2 and Ab3 could be sterically hindered by the analyte-Ab2 binding that form beforehand. In FIG. 1, the primary signal generator has bound to it two second antibodies and, typically, there will be a multiplicity of second antibodies bound to the signal generator. However, some amplification would be achieved even if there were only one antibody attached to each signal generator since the antibody attached to the primary signal generator can bind to the analyte through its $Fab^2$ position and still have sufficient heavy chain exposed, so that the Ab3 antibody attached to the secondary signal generator can bind thereto.

Preferably, both the primary and secondary signal generator will carry multiple antibody, i.e. Ab2 and Ab3 respectively, so that chains 13 comprising both primary and secondary signal generator can form, thereby amplifying the signal generated for each analyte molecule many fold when the chain is immobilized in the detection zone of the solid support by formation of the sandwich between Ab1 the analyte and Ab2.

The solid support can be any of those materials known in the art as being suitable for conducting sandwich immunoassays. Accordingly, the first antibody can be bound to the interior surface of the reaction vessel in which the immunochemical reaction is performed such as in microtitre plates as disclosed in U.S. Pat. No. 4,313,734. Alternatively, solid support can be a strip of porous material through which the test fluid can flow by capillarity as disclosed in U.S. Pat. No. 4,703,017 in which the tracer used in the assay is a ligand labeled with a particulate label which is visible when bound to a binder on the support without further treatment. Thus, in a preferred embodiment the amplified assay of the present invention will be carried out on a porous strip of a material such as filter paper or nitrocellulose having a first region as wicking pad for application of the fluid test sample which flows by capillarity through a second zone containing the labeled anti-analyte (AB2) which is picked up by the fluid test sample. Analyte present in the test sample will react with Ab2 to, form an analyte/labeled antibody conjugate which flows through a third zone containing antibody (Ab3) specific to Ab2 bearing a detectable label as signal generator. Antibody Ab3 is specific only for Ab2 and does not recognize Ab1. This is because the Ab1 band will always give a positive response in the presence of analyte and would not be able to reflect analyte concentration if Ab3 were to bind with Ab2 as well as Ab1. This requirement does not, however, exclude the application of the present amplification method to sandwich assays employing anti-analyte antibodies from the same species as opposed to the use of monoclonal antibodies from the mouse and polyclonal anti-analyte antibodies from a species other than the mouse in the present examples. The amplification method can be used in same species assays by modification of the system. For example, a moiety that is not Ab1, Ab2 or the analyte can be attached to Ab2 and an antibody that recognizes only that moiety is used as Ab3. Alternatively, Fab or $F(ab)_2$ of Ab1 rather than the whole antibody is immobilized on the assay strip and an antibody specific for the heavy chain of Ab2 is used as Ab3. In either of these modified formats, Ab3 forms crosslinks with Ab2 but does not bind with Ab1. The assay can, therefore, be amplified without any unwanted background signal. It is in this step that the amplification takes place by the specific binding of Ab3 with Ab2 to provide at least a doubling of the signal with greater amplification being provided by using signal generator with multiple copies of Ab2 and Ab3 to permit the formation of chains containing a plurality of signal generator. The chains of signal generator bound to the analyte then flow along the strip to the detection zone in which there is immobilized Ab1 which captures the analyte by binding to the epitope of the analyte to which it is specific. The captured analyte produces an enhanced signal due to multiple signal generators being attached to it. As used herein, the terms Ab1, Ab2 and Ab3 are intended to refer to either the intact antibody, and Fab and/or $F(ab)_2$ fragments.

It is possible to form the sandwich before the amplification process, however this requires a more complicated assay system. In one technique employing this embodiment of the invention, in which Ab1 is immobilized, the Ab3-signal generator complex is added to the strip after the analyte-Ab2 is captured by Ab1. This can be accomplished by manual pipetting during the assay process or by controlled release techniques such as by the use of liposomes or microcapsules containing labeled Ab3 in order to delay the binding between Ab2 and Ab3. In a different format the Ab1 is not immobilized, but is instead placed between the regions of the pad containing signal generator coated with Ab2 and secondary signal generator coated with Ab3. In addition, a fourth antibody specific for Ab1 is immobilized on the strip to capture the signal generator chains and produce the assay response.

Figures 2A, 2B:
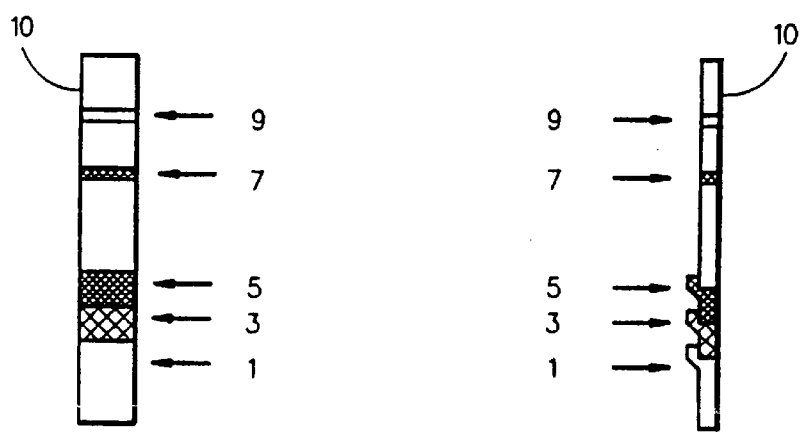
FIG. 2A is a front view and FIG. 2B is a side view of the strip.

The type of strip preferred for use in the present invention is depicted by FIG. 2 in which both front (2A) and side (2B) views are provided. The side view depicts the overlapping of zones which provides greater contact area among the zones and thus facilitates fluid flow in the strip. This is not essential to the operability of the amplification technique of the present invention since simple connections such as head to tail contact are sufficient when the test fluid is one which can flow easily through the strip. In operation in which a test fluid such as urine is being tested for human serum albumin (HSA) a nitrocellulose test strip 10 is used which has a wicking pad 1, a reagent region 3 containing mouse anti-HSA as Ab2 labeled with gold sol and a second reagent region 5 containing goat anti-mouse antibody (Ab3) also labeled with gold sol. Further up the strip is the capture zone 7 in which there is immobilized rabbit anti-HSA (Ab1). The test fluid is applied to the wicking pad where it is absorbed and begins its flow up the strip through zones 3 and 5 and eventually to detection zone 7 where the detectable signal from the signal generator is observed. The space between reagent zone 5 and detection zone 7 is optional but is preferred in order to provide for incubation between the mouse anti-HSA antibody and goat anti-mouse antibody, so that the signal amplifying complexes are fully formed before reaching the detection zone. Optionally, the strip is provided with a positive control zone 9 containing an immobilized specific binding partner for either labeled Ab2 or Ab3, so that the user can determine that the test was operational even in the absence of analyte.

Metal sols, such as the gold sol discussed above, are preferred signal generators, however, any species which will provide a detectable signal to alert the user of the device that analyte has been detected may be employed. Thus, sols of metals other than gold, e.g. silver, palladium or selenium can be used as the primary, secondary or both signal generators. Other signal generators such as a dye filled liposome or microparticle sacs, colored latex particles, enzymes or chromophores can be used as signal generator provided that their attachment to Ab2 does not interfere with the binding between Ab2 and Ab3 such as by masking the heavy chains of Ab2. The use of discrete copies of Ab2 and Ab3 is preferred to enhance the amplification effect.

The absorbant carrier used to prepare the test strip is preferably a filter paper. Other materials useful as the absorbant carrier include felt, porous ceramic strips and woven or matted glass fibers such as those described in U.S. Pat. No. 3,846,247. Also suitable are wood, cloth, sponge material and arillaceous substances such as those described in U.S. Pat. No. 3,552,928. The absorbent carrier should be of a porous material in order to allow the test fluid to migrate by capillary action. In preparation of the strip the absorbent carrier can be impregnated with labeled Ab2 and Ab3 respectively by direct pipetting and air drying followed by the attachment to a trycite backing with double sided adhesive. With the availability of sufficient reagent, a dip method can be used. The method of practicing the present invention is further illustrated by the following examples.

EXAMPLE I

The amplification method of the present invention was demonstrated by a model system using human serum albumin (HSA). The system involved a porous nitrocellulose strip suitable for the flow of fluid test sample by capillarity which strip comprised the following regions: a) a wicking pad; b) a zone containing a gold sol labeled monoclonal antibody; c) a gold sol labeled polyclonal goat anti-mouse antibody in the next zone and finally d) a zone up flow from zone c which bore immobilized polyclonal rabbit anti-HSA antibody.

The assay was performed by dipping the wicking pad of the strip into phosphate buffered saline containing HSA and leaving the strip in contact with the solution until it was completely wetted. To obtain the assay response, the reflectance of the immobilized antibody area (read zone) was measured by use of a CLINITEK™ 100 spectrophotometer after the strip had been air dried. The goat anti-mouse antibody with the gold sol label served as the signal amplifier. A similar assay without the goat anti-mouse antibody (no amplification) was carried out for comparison with the amplified assay.

Figure 3:
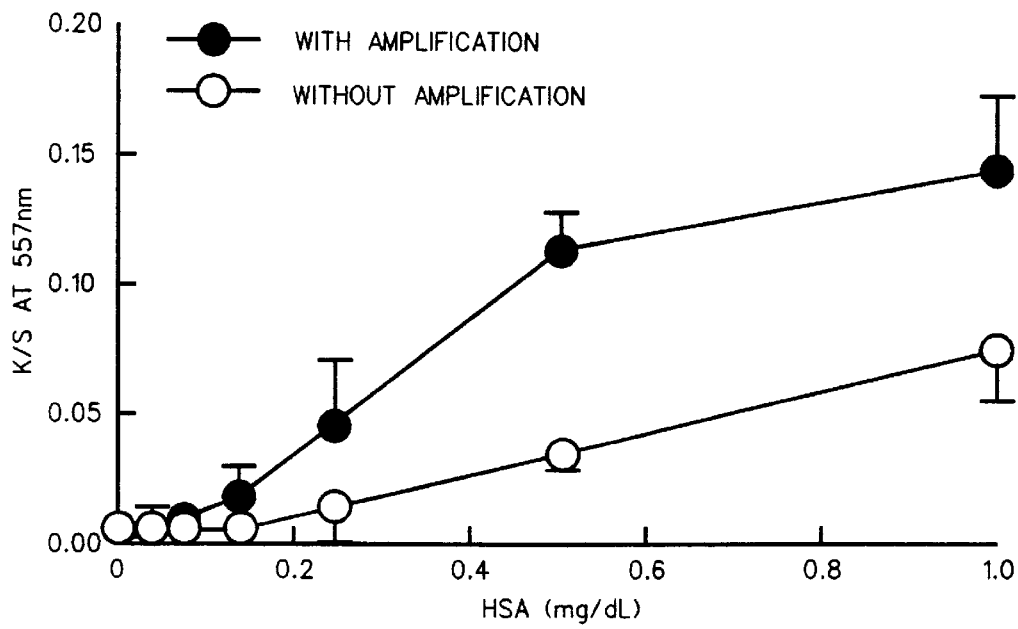
FIG. 3 is a graphical representation of results obtained in the analysis of HSA both with and without the amplification technique of the present invention.

The results obtained from these assays are illustrated by FIG. 3 and demonstrate the feasibility and the following advantages of the amplification method of the present invention:

1) the response of the amplified assay is significantly higher than that for the non-amplified assay;
2) no increase in the background signal is caused by the amplification method; and
3) with improvement in the response signal, the amplified assay is more sensitive than its counterpart.

FIG. 3 represents the dose-response curves of HSA sandwich formats with and without amplification. $K/S=(1-R)^2/2R$ where R=% reflectance. The data presented in FIG. 3 represent the average of 3 replicate runs.

EXAMPLE II

Figure 4:
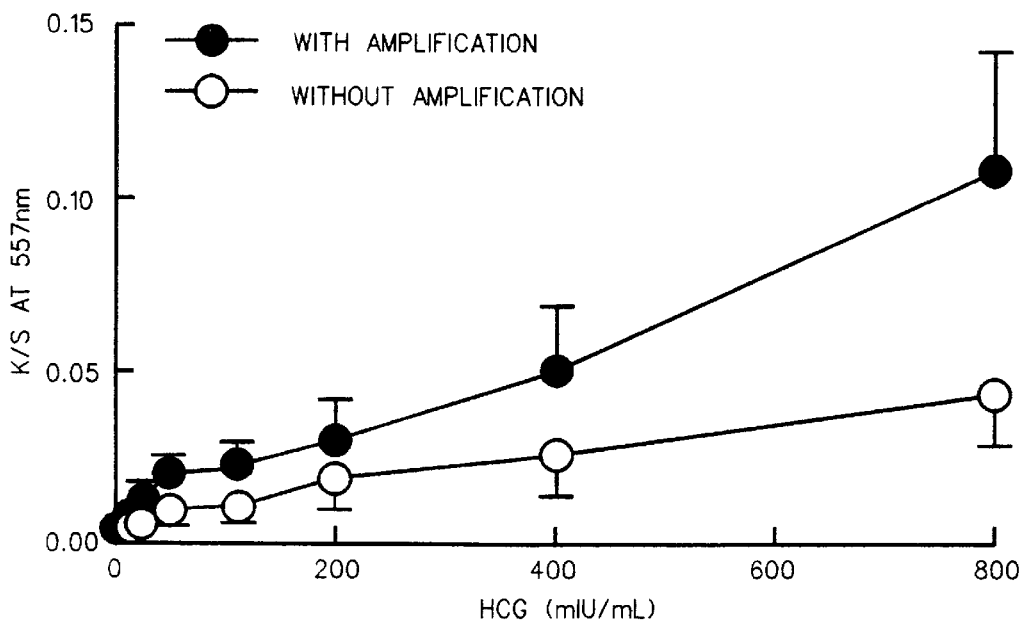
FIG. 4 is a graph representing an assay for hCG both with and without the amplification technique of the present invention.

Similar to the HSA sandwich format, a monoclonal anti-hCG antibody (specific to the hCG alpha-chain) was labeled with gold sol and a polyclonal anti-hCG antibody (raised against the hCG beta-chain) was immobilized on the nitrocellulose membrane. The anti-mouse antibody was again coated onto gold sol and used for signal amplification. The format assembling and assay procedures were the same as in Example I except that 0.5% bovine serum albumin (BSA) was added to the assay solution to protect the activity of hCG. The results of this experiment are represented by FIG. 4.

I claim:

1. In a sandwich type immunoassay in which there is immobilized to a first region of a strip of porous material through which a test fluid suspected of containing an analyte can flow by capillarity a first antibody which is specific for a first epitope of the analyte whose presence or concentration in a liquid test medium is being sought by applying the liquid test medium to the strip and in a second region of the strip there is contained a particulate label which is visible when bound to the strip without further treatment as primary signal generator which has directly bound to it multiple second antibodies which are specific to a second epitope of the analyte, the improvement which comprises including in the second region of the strip a secondary signal generator which is also a visible particulate label having attached to it multiple third antibodies which are specific for the second antibody attached to the primary signal generator but not specific for the parts of the second antibody which comprise the analyte binding sites which third antibody specifically binds to the second antibody to form signal amplifying complexes, and allowing the second labeled antibody and third labeled antibody to interact with each other and the analyte to form signal amplifying complexes to amplify the signal generated when the first immobilized antibody specifically binds with the first epitope of the analyte when the liquid test medium containing the signal amplifying complex of the second antibody, third antibody and analyte flow into the first region of the strip by capillarity to thereby bind the signal amplifying complex to the first region of the strip to thereby provide an amplified detectable signal in the first region of the strip.

2. The improvement of claim 1 wherein the primary and secondary signal generators are the same.

3. The improvement of claim 2 wherein the primary and secondary signal generators are colored, colloidal sized particles.

4. The improvement of claim 3 wherein the colloidal sized particles comprise a metal sol.

5. The improvement of claim 4 wherein the metal is gold.

6. The improvement of claim 1 wherein the antibody attached to the secondary signal generator is specific to the heavy chain of the antibody which is attached to the primary signal generator.

7. The improvement of claim 1 wherein the test fluid is urine and the analyte is hCG.

8. The improvement of claim 1 wherein one or more of the antibodies is a complete antibody.

9. The improvement of claim 1 wherein one or more of the antibodies is a Fab or $F(ab)_2$ fragment.

10. A test strip for the detection of an analyte in a test fluid which strip is made of an absorbant material through which the test fluid can flow by capillarity which strip has immobilized to a first region thereof a first antibody specific for a first epitope of the analyte and which strip has absorbed therein in a second region distinct from the first region a second labeled antibody which is specific to an epitope of the analyte different than that to which the immobilized antibody is specific and a third labeled antibody which is specific to the second labeled antibody but not specific for the parts of the second antibody which comprise the analyte binding sites and wherein the label is a particulate label which is visible when bound to the strip without further treatment which particulate labels have respectively multiple second and third antibodies bound to them, so that when the test fluid is applied to the strip it flows along the strip by capillarity and analyte contained in the test fluid binds with the second labeled antibody and third labeled antibody to form a signal amplifying complex which complex flows by capillarity to the first region of the strip and binds with the first immobilized antibody to form a sandwich comprising the analyte bound between the immobilized antibody and the second labeled antibody which sandwich provides an amplified detectable signal due to the the formation of the signal amplifying complex in the second region of the strip.

11. The strip of claim 10 wherein the first and second labeled antibody are labeled with colored colloidal sized particles.

12. The strip of claim 11 wherein the colloidal sized particles comprise a metal sol.

13. The strip of claim 12 wherein the metal is gold.

14. The strip of claim 10 wherein the third labeled antibody is specific to the heavy chain of the second labeled antibody.

15. The strip of claim 10 wherein the analyte to which the second labeled antibody and the immobilized antibody are specific is human serum albumin.

16. The test strip of claim 10 wherein the analyte to which the second labeled antibody and the immobilized antibody are specific is hCG.

17. The strip of claim 10 wherein one or more of the antibodies is a complete antibody.

18. The strip of claim 10 wherein one or more of the antibodies is a Fab or F(ab)$_2$ fragment.

19. A test strip for the detection of an analyte in a test fluid which comprises an absorbant carrier material through which the test fluid can flow by capillarity which strip comprises:

a) a reagent region containing a second labeled antibody which is specific to an epitope of the analyte;

b) a second reagent region containing a third labeled antibody which is specific to the second labeled antibody but not specific to the parts of the second antibody which comprise the analyte binding sites and wherein the label on the second and third antibodies is a particulate label which is visible when bound to the strip without further treatment which particulate labels have respectively multiple second and third antibodies bound to them so that the second labeled antibody, third labeled antibody and analyte in the test fluid can form a signal amplifying complex upon application of an analyte containing test fluid to the strip; and c) a capture zone into which the signal amplifying complex can flow by capillarity in which there is immobilized a first antibody specific to an epitope of the analyte different than that to which the second labeled antibody is specific so that when the signal amplifying complex flows into the capture zone, it is captured by the first antibody to thereby provide an amplified signal in the capture zone.

20. The strip of claim 19 which also contains a wicking region adjacent to the first reagent region for application of the test fluid.

21. The strip of claim 19 which also contains a positive control zone located downstream from the capture zone which contains an immobilized specific binding partner for the second or third labeled antibody.

22. The strip of claim 19 wherein one or more of the antibodies is a complete antibody.

23. The strip of claim 19 wherein one or more of the antibodies is a Fab or F(ab)$_2$ fragment.

24. The strip of claim 21 wherein the first and second reagent zones overlap so that the second and third labeled antibodies are intermixed in the dry strip.

* * * * *